United States Patent [19]

Lange, III et al.

[11] Patent Number: 5,432,058
[45] Date of Patent: Jul. 11, 1995

[54] METHOD FOR MEASURING HUMAN CHOLESTEROL ABSORPTION USING METABOLICALLY STABLE ISOTOPES

[76] Inventors: Louis G. Lange, III, 390 Escobar Rd., Portola Valley, Calif. 94028; Richard E. Ostlund, 39 Fair Oaks, Ladue, Mo. 63124; Matthew S. Bosner, 14330 Wainridge, Chesterfield, Mo. 63110

[21] Appl. No.: 954,864

[22] Filed: Sep. 30, 1992

[51] Int. Cl.⁶ .................. C12Q 1/60; G01N 31/00; A01N 43/04
[52] U.S. Cl. .................. 435/11; 435/19; 435/968; 436/13; 436/16; 436/56; 436/57; 436/504; 436/804; 424/1.11; 424/529; 424/530; 514/54; 514/55; 514/57; 514/59
[58] Field of Search .......... 435/11, 19, 968; 436/13, 16, 56, 57, 504, 804; 424/1.11, 529, 530; 422/71; 210/656, 682; 514/54, 55, 57, 59

[56] References Cited

U.S. PATENT DOCUMENTS

| 4,066,829 | 1/1978 | Nair et al. | 536/103 |
|---|---|---|---|
| 4,150,110 | 4/1979 | Yoshida et al | 424/33 |
| 5,017,565 | 5/1991 | Lange, III et al. | 514/54 |

OTHER PUBLICATIONS

McNamara et al., *J. Clin. Invest.*, vol. 79, pp. 1729–1739, 1987.
Eckfeldt et al., *Clin. Chem.*, vol. 37, No. 7, pp. 1161–1165, 1991.
Veares et al., *Chemical Abstracts*, vol. 114, p. 357, Ref. No. 20410; 1991 (Biomed. Environ. Mass Spectrum 19 (10), 1990).
Zilversmit, D. B., Proc. Soc. Exp. Med. Biol. 140:862–865 (1972).
Zilversmit and Hughes, J. Lipid Res. 15:465–473 (1974).
Samuel et al., J. Lipid Res. 19:82–93 (1978).
Samuel et al., J. Lipid Res. 23:480–489 (1982).
Crouse et al., J. Lipid Res. 24:854–860 (1983).
McNamara et al., J. Clin. Invest. 79:1729–1739 (1987).

*Primary Examiner*—Michael G. Wityshyn
*Assistant Examiner*—Abdel A. Mohamed
*Attorney, Agent, or Firm*—Allegretti & Witcoff, Ltd.

[57] ABSTRACT

This invention is a method for measuring the ability of a human to absorb cholesterol. The method uses two different cholesterol tracers, the first injected into the blood stream and the second ingested by the human subject. After a waiting period a blood sample is taken from the human subject and analyzed to determine percent cholesterol absorption based on the actual amounts of the two naturally occurring, metabolically stable cholesterol tracers in the blood. The method of this invention is useful in identifying human subjects as high cholesterol absorbers and thereafter administering therapeutic agents to the subject that inhibit the absorption of cholesterol.

14 Claims, 3 Drawing Sheets

METHOD FOR MEASURING HUMAN CHOLESTEROL ABSORPTION USING METABOLICALLY STABLE ISOTOPES

BACKGROUND OF THE INVENTION

Portions of this invention were supported by National Institute of Health Grant R01 HL 29229. The Government has certain rights to this invention.

(1) Field of the Invention

This invention concerns a method for measuring the ability of a human to absorb cholesterol and the use of the method to treat high cholesterol absorbers. The method uses unique injected and ingested naturally occurring, metabolically stable cholesterol tracers and measures the relative amounts of both of the cholesterol tracers in the blood of a human subject after a waiting period.

Dietary cholesterol restriction is an important part of therapy for many forms of hyperlipidemia as well as a general recommendation for the public. However, the relation between atherosclerosis and the diet needs further, investigation. Previous studies of dietary cholesterol absorption have focused on middle-aged men, often with hyperlipidemia or atherosclerosis, and have used radioactive methods. These data may not be applicable to other populations. In addition, the use of radioactivity generally precludes the study of women and children making a thorough analysis of the clinical genetics of cholesterol absorption impossible.

The method of this invention is ideal for determining cholesterol absorption because it uses only plasma cholesterol measurements and avoids both the inconvenience and increased analytical variability associated with stool collection. Such a method was proposed by Zilversmit, but was based upon cholesterol labeled with tritium (administered intravenously) and carbon-14 (given orally). Isotopic ratio determination in plasma after 3 days of equilibration in the rapidly-miscible pool of body cholesterol provides an estimation of fractional absorption. During this time period, a negligible amount of cholesterol tracer is excreted from the body. Such an isotope ratio method has been validated in man by comparison to other methods including those that involve oral administration of radiolabeled cholesterol and stool collection.

We have developed a novel approach to measure cholesterol absorption in humans using stable isotopic derivatives of cholesterol. Cholesterols labeled with either deuterium or carbon-13 to achieve a mass difference of 5 or 6 daltons over natural cholesterol are administered in small amounts (15–30 mg) that are easily detected in the blood by gas chromatography mass spectrometry (GC/MS).

(2) Description of the Art

Although national recommendations for consumption of dietary cholesterol have been issued in several countries, there are remarkably few data available on measurement of cholesterol absorption in normal humans. Most studies have been performed using middle-aged male subjects with hyperlipidemia or coronary heart disease, and conclusions based on these small and selected groups may not be applicable to the population at large. Although recent reports of cholesterol absorption involving substantial numbers of normal men aged 44–55 have been published, there is much less information about other age groups.

Cholesterol absorption studies of women are rare and no studies of infants or children have been done. The effect of the amount of dietary fat on cholesterol absorption is also not yet settled. Although there are several reasons for the reluctance to study cholesterol absorption, the need to use potentially hazardous radioactive isotopes is an important factor, in the lack of such data especially in younger individuals and women of child bearing years.

The use of radioactive labeled cholesterols to measure human cholesterol absorption using an isotope ratio method is well known in the art. The method was first described in Zilversmit, PSEBM; 140:862–65 (1972), and Zilversmit et al., J. Lipid. Res.; 15:465–73 (1974) which describe the use of radiolabeled isotopes of cholesterol to determine cholesterol absorption in rats.

The Zilversmit dual isotope method has been successfully applied to determine human cholesterol absorption as described in various references including Samuel et al., J. Lipid Res.; 19:82–93 (1978); Samuel et al., J. Lipid Res.; 23: 480–489 (1982); and Crouse et al., J. Lipid Res.; 24:854–860 (1983).

The Zilversmit method is still used for various cholesterol absorption protocols. For example, McNamara et al., J. Clin. Invest.; 79; 1729–1739 (1987) used the Zilversmit method to examine the effects of dietary fat on cholesterol hemostasis in man. However, the Zilversmit method's primary drawback is its use of radioactive labeled cholesterols. Such labeled cholesterols present unknown dangers to human subjects and preclude the use of the dual isotope method on pregnant women and children. Additionally, the method usually requires focal analysis as well as blood serum analysis. Both of these drawbacks to the Zilversmit method are avoided by the method of this invention.

SUMMARY OF THE INVENTION

It is an object of this invention to provide a dual isotope method for measuring human cholesterol adsorption that eliminates the need to use radioactive cholesterol tracers.

It is another object of this invention to provide a method for measuring human cholesterol absorption that can be performed on pregnant women and children.

It is still another object of this invention to provide a method for measuring human cholesterol absorption that does not require the measurement of fecal cholesterol.

In one embodiment, this invention is a method for measuring the ability of a human to absorb cholesterol. The method comprises the steps of injecting a first metabolically stable cholesterol into the blood stream of a human subject. Next, a second metabolically stable cholesterol is introduced into the human subject by ingestion. After waiting for from about 12 hours to about 5 days or more, a blood sample is withdrawn from the human subject and analyzed to determine the relative amount of the first naturally occurring metabolically stable cholesterol and the second naturally occurring metabolically stable cholesterol in the blood sample.

In another embodiment, this invention is a method for measuring the ability of a human to adsorb cholesterol. The method comprises injecting $[23,23,25,26,27]$-$^{13}$C-cholesterol into the blood stream of a human subject and introducing $[26,26,26,27,27,27]$-$^2$H-cholesterol into the digestive system of the human subject by ingestion. A blood sample is withdrawn from the human subject after waiting for from about 24 hours to about 96 hours. The blood sample is analyzed by GC/MS in order to obtain relative concentration data on the amount of [23,23,25,26,27]-$^{13}$C-cholesterol and [26,26,26,27,27,27]-$^{2}$H-cholesterol in the blood sample. Finally, the relative concentration data is corrected to obtain actual cholesterol tracer concentration data and the percentage of the first cholesterol tracer absorbed by the subject.

In still another embodiment, this invention is a method for treating a human subject who is a high absorber of cholesterol. The human subject is first tested by the method of this invention in order to identify them as a high absorber of cholesterol. The testing method comprises the steps of injecting a first metabolically stable cholesterol into the blood stream of a human subject and allowing the human subject to ingest a second metabolically stable cholesterol. After waiting for from about 12 hours to about 5 days or more, a blood sample is withdrawn from the human subject and analyzed to determine the relative amount of the first metabolically stable cholesterol and the second metabolically stable cholesterol in the blood sample are. If the human subject is determined to be a high cholesterol absorber, then they are administered an effective amount of a cholesterol absorption inhibiting agent.

DESCRIPTION OF THE DRAWINGS

There is shown in the drawings presently preferred embodiments of the tracer cholesterol of this invention wherein.

Figure 1:
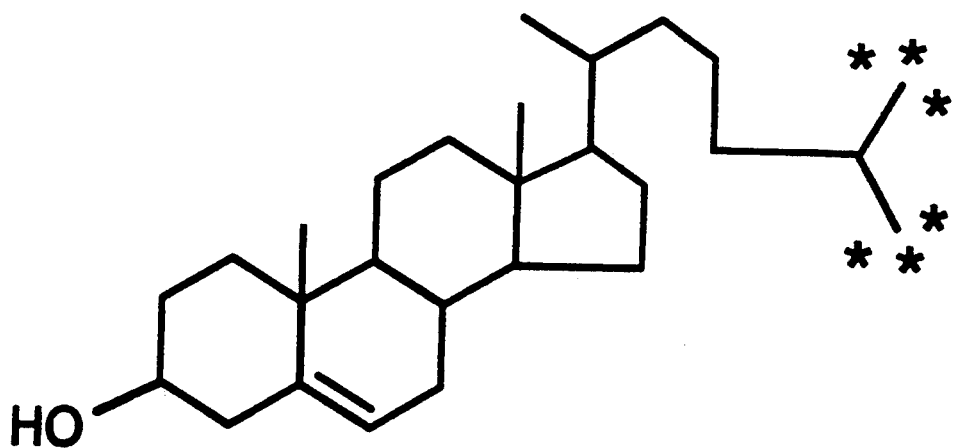
FIG. 1 is [26,26,26,27,27,27]-$^{2}$H-cholesterol.
Figure 3:
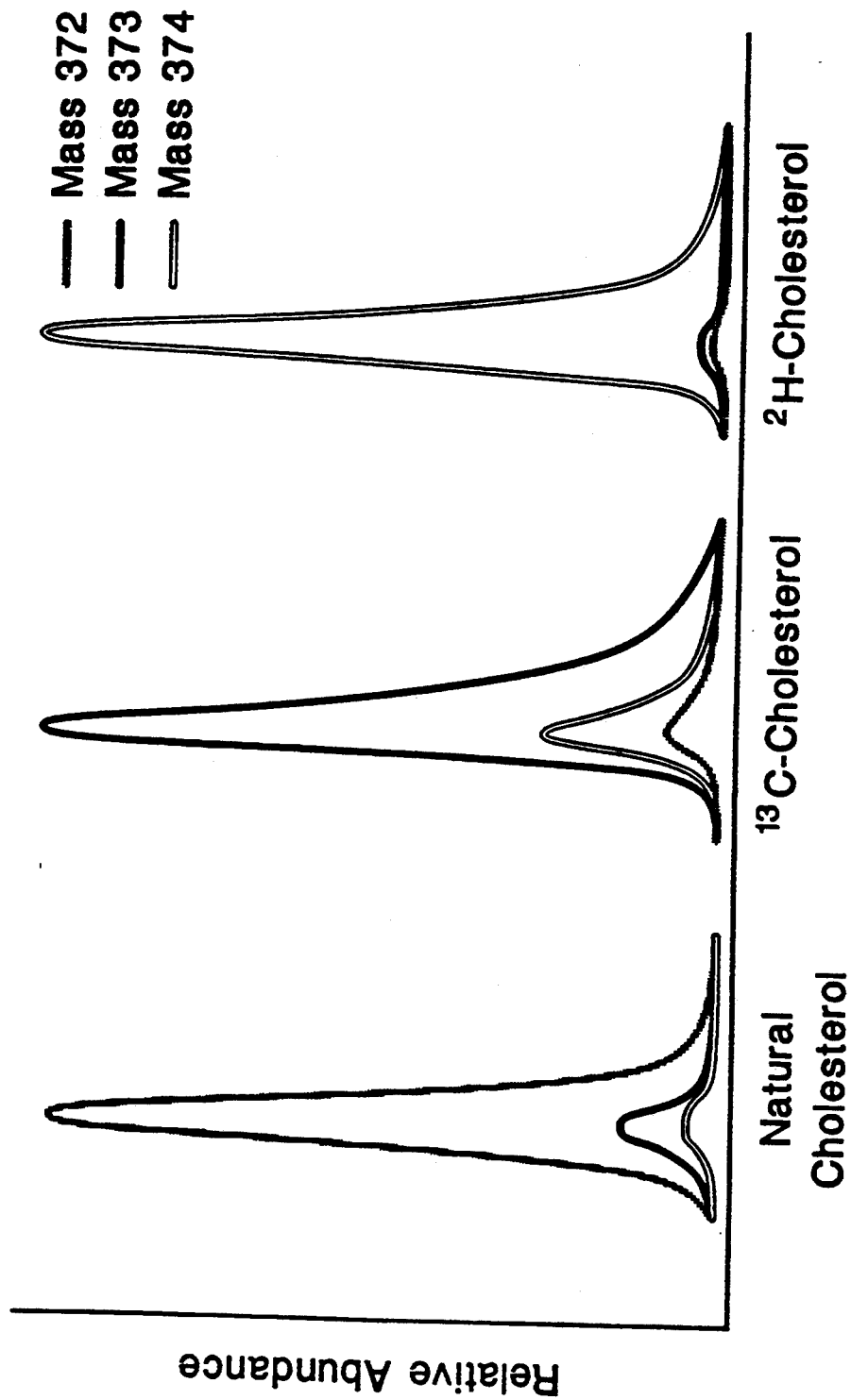
Figure 4:
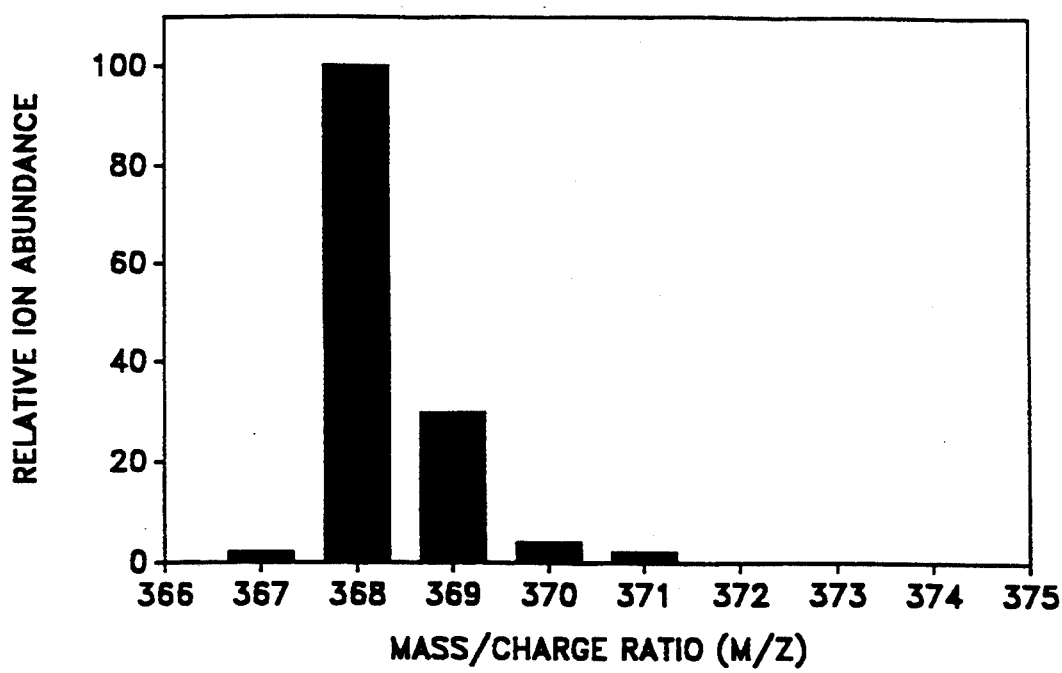
Figure 5:
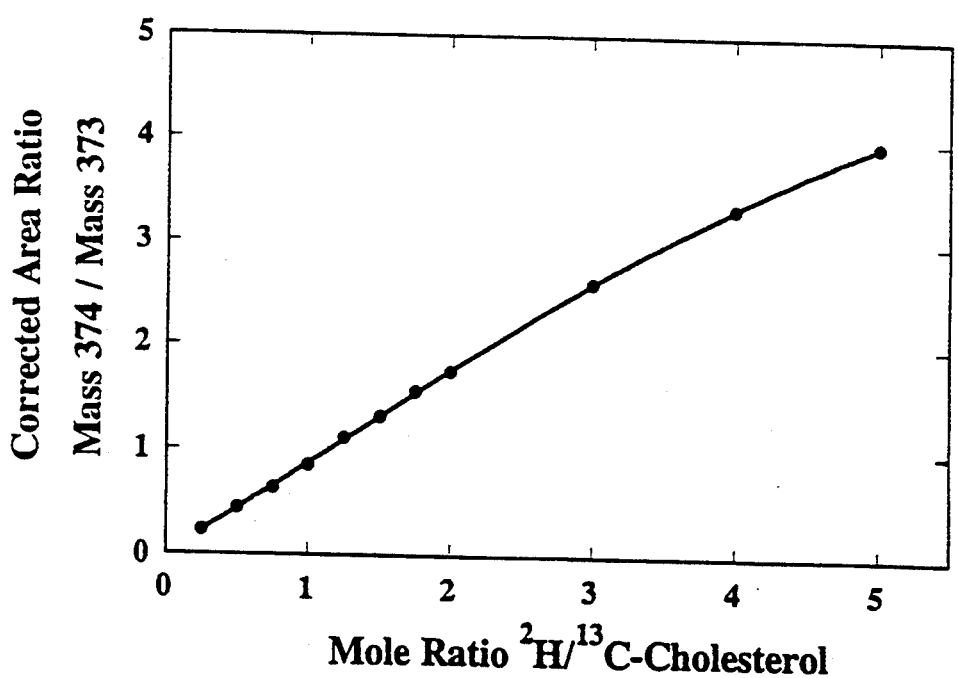

Additionally, there is shown in the drawings various plots relating to the identification of the tracers of this invention by GC/MS techniques wherein;

FIG. 3 is a plot of the relative abundance of ions generated from cholesterol acetate;

FIG. 4 is a standard curve relating the corrected area ratio derived from selected ion monitoring to weighted mole ratio of tracer cholesterol; and FIG. 5 is a standard curve relating to corrected area ratio derived from selected ion monitoring to weighted mole ratio of tracer cholesterols of this invention.

DESCRIPTION OF THE CURRENT EMBODIMENT

The present invention relates to a method for measuring cholesterol absorption in humans and a method for identifying and treating humans who are high cholesterol absorbers. The method measures the percentage of a cholesterol tracer that is absorbed or transferred from the human digestive system to human blood serum.

There is a paucity of information concerning cholesterol absorption in humans, and one prominent reason for this deficiency is the need to administer long-lived radioactive cholesterol tracers. To eliminate this hazard, we have developed a procedure, based on that of Zilversmit (Prof. Soc. Exp. Med. Biol. 140:862–865, 1972), employing stable isotopic tracers of cholesterol. One metabolically stable cholesterol tracer is administered orally and a second metabolically stable cholesterol tracer is administered intravenously on day 0. The ratio of the two tracers is determined after equilibration on about day 3 by gas chromatography-mass spectrometry (GC/MS) with selected ion monitoring. Ion current peaks corresponding to the first and second tracers are corrected for spillover From each other and from endogenous cholesterol. Percent cholesterol absorption is calculated as the ratio of the cholesterol tracers. The use of stable cholesterol isotopes for the study of cholesterol absorption is feasible, precise, safe and allows broad application of cholesterol absorption measurements in humans including women and children, thereby Facilitating clinical genetic studies in groups about which little current data is available.

When the relation between cholesterol and atheroselerosis is considered, the usual focus of attention is on plasma cholesterol concentration, which comprises less than 9% of total body cholesterol. Thus, insights from whole body cholesterol metabolism complements and extends those obtained from the extensive literature on plasma lipoprotein cholesterol. Cholesterol absorption from the gastrointestinal tract is a key component of whole body cholesterol metabolism, not only because of dietary cholesterol content, but also because of the two-fold larger enterohepatic recirculation of endogenous cholesterol which readily mixes with dietary cholesterol to form a single pool of intestinal cholesterol. The percent of cholesterol absorbed varies from 15% to 75% in humans, a broad range suggestive of metabolic or genetic regulation. However, that hypothesis has not been thoroughly tested biochemically or clinically and relatively little information is available on important aspects of cholesterol absorption, especially in normal subjects and women.

The labeling of cholesterols with stable isotopes has been accomplished previously but complicated clinical protocols were employed. In particular the measurement of $^{13}$C-cholesterol had to be carried out by isotope ratio mass spectrometry, an extraordinarily precise technique but one which is somewhat cumbersome and requires isolation of pure cholesterol and its combustion to $CO_2$ before analysis. Deuterium enrichments were measured separately. In contrast, the current GC/MS technique is much simpler in that conventional gas chromatography is performed and the mass spectrometer is used as a mass-sensitive detector capable of measuring both cholesterol tracers at the same time. The current method can be performed reliably with 15–30 mg of orally administered labeled cholesterol, an amount which, while greater than a normal tracer dose, is still relatively small compared to the recommended daily intake of cholesterol of 300 mg.

The cholesterol tracers useful in this invention arc naturally occurring and metabolically stable in that they are essentially inert in the human body. The naturally occurring cholesterol tracers used however are substituted with a sufficient amount of deuterium, ($^{2}$H) or $^{13}$C to give the useful cholesterol tracers a mass difference of 5 or 6 daltons greater than the corresponding natural cholesterol.

Figure 2:
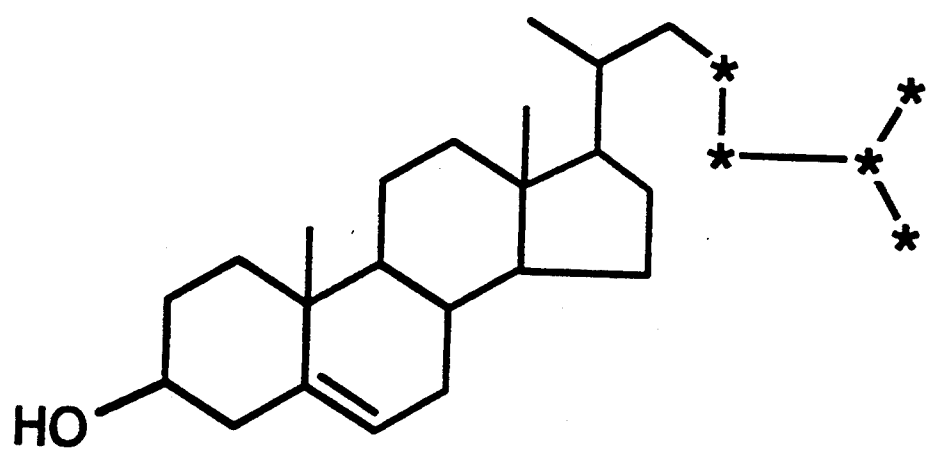
FIG. 2 is [23,24,25,26,27]-$^{13}$C-cholesterol.

Two preferred metabolically stable cholesterol tracers are [23,24,25,26,27]-$^{13}$C-cholesterol as shown in FIG. 2 and [26,26,26,27,27,27]-$^{2}$H-cholesterol shown in FIG. 1. It is not critical which of the two preferred cholesterol tracers is ingested and which is injected into the blood stream of a human subject. What is most important is that the two tracers are simultaneously differentiated by GC/MS techniques, and that the two tracers, a first tracer and a second tracer are different compounds.

There is a waiting period after the cholesterol tracers of this invention have been administered to a human subject. The waiting period allows the ingested cholesterol tracer to reach equilibrium in the subject's blood. The waiting period can range from 12 hours to about 5 days or more. However, it is preferred that the waiting period is from about 24 hours to about 96 hours. Following the waiting period, a blood sample is withdrawn from the subject and analyzed by GC/MS techniques to determine the relative amount of the two cholesterol tracers and the natural cholesterols in the sample. The GC/MS data is corrected to provide the actual relative amounts of the cholesterol tracers in the blood sample and a cholesterol absorption percentage is calculated based upon the amount of cholesterol tracers introduced into the body in relation to the amount in the blood samples.

The method of this invention is useful for performing repeated studies in the same individual with small inter-test differences (standard deviation=2.8%) enabling dietary and other interventions to be studied in detail with excellent results. The present modification of the Zilversmit Dual Isotope method allows cholesterol absorption to be determined in human test groups that are representative of the general population.

An important aspect of this invention is the analysis of samples of blood containing equilibrated amounts of two cholesterol tracers of this invention. When natural cholesterol acetate is subjected to electron ionization mass spectrometry, a prominent ion was found at mass 368, representing dehydrated cholesterol after loss of acetic acid from the original ester 1 as shown in FIG. 3. In contrast, as shown in FIG. 3, comparatively little signal was observed at masses 373 and 374. Therefore, the use of metabolically stable cholesterols 5 or 6 daltons greater in mass than that of natural cholesterol are used is the screening method to reduce the interference from endogenous cholesterol.

The importance of this step can be appreciated by considering that the tracers are diluted into a rapidly-miscible body cholesterol pool of approximately 24,000 mg. In typical mass spectrometric assays the ratio of tracer to natural material is determined, but that is not usually practical because of the large mass of natural cholesterol found in humans. Moreover, the only information needed is the actual ratio of the two tracer molecules in plasma. Therefore, the large peak of natural cholesterol at mass 368 is ignored and the non-abundant but reproducibly present and similar quantities of ions at masses 372 (representing principally natural cholesterol), 373 ($^{13}C$-cholesterol), and 374 ($^{2}H$-cholesterol) is measured instead.

After the injection of either natural cholesterol or labeled cholesterol in the GC/MS apparatus, various area responses are observed at different masses as shown in FIG. 4. Natural cholesterol gives a peak at mass 372 with much smaller but still appreciable peaks at 373 and 374. The distribution and relative amounts of each of these ions (masses 372, 373 and 374) are highly consistent in the same individual. Likewise, the spillover from $^{13}C$-cholesterol and $^{2}H$-cholesterol to other masses is consistent. By using simultaneous equations the measured peak areas of $^{13}C$-cholesterol and $^{2}H$-cholesterol are corrected for spillover from each other and from endogenous cholesterol. These corrected peak areas are then related to known weighed mixtures of the tracers in a standard curve as shown in FIG. 5. The ratio of tracer cholesterols in an unknown sample can then be derived from the standard curve. When replicate extractions and GC/MS measurements of the same sample are performed on different days, the coefficient of variation in the computed values of tracer ratios read from standard curves is 1.9%.

This invention also involves administering a therapeutic amount of human cholesterol inhibiting agent to a human who has been identified as a high cholesterol absorber by the method of this invention. For purposes of this invention, a person is deemed to be a high absorber of cholesterol when the method of this invention indicates that they have absorbed 50% or more of the ingested cholesterol tracer. This threshold value however may vary depending on such factors as the age, sex, dietary and medical history of the person tested.

A person who is identified as a high absorber of cholesterol may be treated with a therapeutic amount of known intestinal cholesterol absorption blocker. One agent in particular, sulfated polysaccharides are preferred. Sulfated polysaccharides inhibit the absorption of pancreatic cholesterol esterase.

A variety of polysaccharide polymers that exist in nature can be sulfated to produce potent inhibitors of human pancreatic cholesterol esterase. Such polysaccharide can be derived in a controlled manner from a variety of abundant and cheap polysaccharides such as alginic acid (from seaweed), pectin (from vegetables and fruit), chitin (from mollusks), dextrans and cellulose (from plants and trees) to produce sulfated derivatives. These derivatives are all soluble, potent inhibitors of human pancreatic cholesterol esterase, whereas the parent starting polymers are either not inhibitory or poorly inhibitory. The manufacture and use of such inhibitors is described in U.S. Pat. No. 5,017,565 which is incorporated herein by reference. In addition, sulfated amylopectin is an effective inhibitor of cholesterol esterase. Amylopectin sulfate and its uses as a pharmaceutical agent is described in U.S. Pat. Nos. 4,150,110 and 4,066,829, also incorporated herein by reference.

While a number of structural features of the inhibitory agents can modulate the degree of inhibition, the presence of a 3-sulfate markedly enhances inhibition. In essence, naturally occurring polysaccharide polymers, often regarded as waste, can be converted into a series of highly potent, cheap, nonabsorbed and non-toxic inhibitors of cholesterol and fatty acid absorption that can be administered as a soluble agent in small and well-tolerated quantities.

These sulfated polysaccharide inhibitors of cholesterol esterase can be administered in pharmaceutical dosage forms such as tablets, capsules, liquids, and powders. They also can be incorporated with food products such as biscuits and cookies. The sulfated polysaccharides are used as a dietary supplement to reduce cholesterol and fatty acid absorption. Those skilled in the food and pharmaceutical arts will recognize a wide variety of formulations and vehicles for administering sulfated polysaccharides. Preferably, sulfated polysaccharides are administered with food or about the time of food intake.

The invention is illustrated further by the following examples which are not to be construed as limiting the invention in scope or spirit to the specific procedures described in them.

EXAMPLE 1

This example identifies the source of and discusses the characteristics of metabolically stable cholesterol tracers useful in this invention.

[23,24,25,26,27]-$^{13}C$-cholesterol with average substitution of 99% at each enriched site was synthesized by Dr. Alfred Ajami of Tracer Technology, Inc. The chemical formula is shown in FIG. 1. The material as supplied contained 26% [23,24,25]-$^{13}$C-[26,27]-bisnorcholesterol, a phytosterol missing two terminal methylene groups. For some studies and preparation of standards, this impurity was removed by HPLC using an octadecyl reversed phase column eluted with methanol for preparation of standards and for some studies. However, purification was not routinely necessary since the impurity is not measured in the GC/MS analysis.

[26,26,26,27,27,27]-$^{2}$H-cholesterol shown if FIG. 2 was prepared by Dr. Eric Stohler of Biodesign, Inc. The deuterium in the labeled cholesterol is located on stable terminal methyl groups of the side chain. When both: $^{13}$C-cholesterol and $^{2}$H-cholesterols were given intravenously or orally to rabbits there was no change in the plasma ratio of the two cholesterols over one week.

EXAMPLE 2

This example explores the use of metabolically stable cholesterol tracers to evaluate human cholesterol absorption.

Five healthy subjects (three men and two women, age 22–34) underwent two cholesterol absorption studies separated by 4–6 weeks. Out patient subjects received a National Cholesterol Education Program step I diet prepared in the metabolic kitchen of the Washington University Clinical Research Center for five days. Starting two days before testing and ending three days after testing. The metabolically stable cholesterols were given on day 0 with a meal containing 240 ml of whole milk as a source of fat to assure contraction of the gallbladder.

[23,24,25,26,27]-$^{13}$C-cholesterol suitable for intra venous administration was prepared in a laminar flow hood. The labeled cholesterol was dissolved at 5 mg/ml in USP ethanol in a sterile container, water was added to 10% by volume in order to increase virucidal activity, and the solution was allowed to stand at room temperature for at least 6 hrs. The solvents were then sterilely removed and the cholesterol residue dissolved at 20 mg/ml in ethanol and passed through a 0.22 micron solvent-resistant filter. Aliquots were tested for sterility and dried aliquots for pyrogenicity using the Limulus assay, and the stock was kept frozen at −70° C. On the day of the experiment both the $^{13}$C-cholesterol and a small amount of 10% Intralipid were warmed to 37° C. and the ethanolic cholesterol was added dropwise to 4 volumes of Intralipid. After 5 minutes at 37° C. and 15 min. at room temperature the mixture was put through a 0.8 micron particulate filter. More than 94% of the labeled cholesterol passed through the filter. An aliquot containing approximately 15 mg. $^{13}$C-cholesterol was drawn into atared syringe and weighed. The syringe contents were injected over 5 minutes into a running saline infusion and the syringe was washed several times with saline. With the use of Intralipid, cholesterol is quantitatively solubilized and less than 0.4% of the tracer cholesterol is found in the syringe and intravenous lines.

Deuterated cholesterol for oral administration was dissolved in corn oil at 15 mg/ml and stored at −70° C. An English muffin was dried to stable tare weight and an amount of the warmed oil solution containing approximately 30 mg tracer was added dropwise on an analytical balance. The muffin was given with breakfast on day 0. The mole ratio of tracer cholesterols administered was determined by mixing and analyzing precisely weighed aliquots of the [23,24,25,26,27]$^{13}$C-cholesterol-Intralipid infusate and oral corn oil stock. It was not necessary to determine precisely the milligram amounts of cholesterol tracers given and this was not routinely done. Calculations depend only on weighed variables and area ratios of selected ions derived from the mass spectrometer.

Total cholesterol (about 2 mg) was purified from 1 ml EDTA-anticoagulated plasma by saponification of the sample in ethanolic base and extraction of the nonsaponifiable sterols into petroleum ether according to Goodman et al., J. Clin. Invest.; 47:231–241 (1968). Acetate esters of cholesterol were prepared by dissolving approximately 400 µg cholesterol in 160 µl anhydrous pyridine, adding 800 µl acetic anhydride, mixing, and allowing the solution to stand overnight at room temperature. Volatile reagents were removed and the solid cholesterol acetate was taken up in heptane at a concentration of 5 mg/ml. Approximately 5 µg was injected onto a 122 em packed column of 1% SE-30 at 250° C. and admitted to a Finnigan 3300 mass spectrometer operating in electron ionization mode with a quadruple mass analyzer. Selected ions were monitored at m/z=372, 373, and 374. The amount of cholesterol injected was the largest amount that did not saturate the mass spectrometer source.

Each day a standard curve was generated using weighed samples with known mole ratios of the $^{2}$H/$^{13}$C-cholesterol tracers of this invention diluted in natural cholesterol. An example of such a curve is found in FIG. 5. Plasma cholesterol samples from each subject taken before and three days after isotope administration were also analyzed. The resulting GC/MS raw peak areas at masses 372, 373 and 374 represent principally natural cholesterol, the $^{13}$C-cholesterol tracer, and the $^{2}$H-cholesterol tracer, respectively, but with some overlap from the other species. Corrected peak areas were calculated as the peak areas at each of these masses due to the principal species alone after subtraction of overlapping signals. This was accomplished by solving 3 simultaneous equations each expressing an observed ion current peak area as a function of contributions from unknown amounts of the three cholesterols (X, Y and Z variables) using the Simulation, Analysis, and Modeling (SAAM) computer program obtained from the resource Facility for Kinetic Analysis at the University of Washington. The constants for these equations were determined :using pure tracers and from the pre-injection plasma cholesterol sample. Natural cholesterol contributed less than 10% of the signal observed at the masses of the labeled cholesterols. The corrected ion current area ratio of labeled tracer cholesterols in plasma was then compared to a standard curve to yield the mole ratio of tracer cholesterols.

Results of cholesterol absorption studies in five healthy subjects who underwent a second cholesterol absorption study 4–6 weeks after an initial determination demonstrated minimal variation as shown in Table I.

TABLE I

| Subject | Sex | BMI (Kg/m2) | TC | LDL | HDL | TG | Test 1 | Test 2 |
|---|---|---|---|---|---|---|---|---|
| 1 | F | 61.1 | 223 | 150 | 57 | 58 | 59.4 | 62.4 |
| 2 | F | 68.4 | 192 | 127 | 62 | 82 | 62.2 | 58.0 |
| 3 | M | 61.8 | 172 | 110 | 52 | 63 | 70.5 | 67.2 |
| 4 | M | 68.4 | 162 | 104 | 33 | 130 | 47.4 | 45.4 |
| 5 | M | 29.4 | 202 | 134 | 46 | 84 | 57.1 | 55.0 |
|  |  |  |  |  |  |  | 59.3 ± 8.4 | 57.6 ± 8.2 |

In Table I, BMI represents the body mass index of each subject. TC represents total cholesterol. TG represents triglycerides, and LDL and HDL represent low density lipoproteins and high density lipoproteins respectfully all in mg/dl.

The mean cholesterol absorption was 59% in test I with a range between subjects of 47 to 71%. However, variability in the same individual did not occur, so that over time low absorbers, exhibiting less than about 50% cholesterol absorption remained low absorbers and high absorbers remained high. The standard deviation of the difference between test 1 and 2 was 2.8%, which compares favorably with 3.7% calculated from data reported with the radioactive method. There was no difficulty in performing the repetitive cholesterol absorption studies even though a small amount of tracer cholesterol could be detected in plasma at the time of the second study since this background is accounted for in the analysis of plasma obtained just before the second study.

What we claim is:

1. A method for measuring the ability of a human to absorb cholesterol comprising the steps of:
   a. introducing a known amount of [23,23,25,26,27]-$^{13}$C-cholesterol into the blood stream of a human subject by injection;
   b. introducing a known amount of [26,26,26,27,27,27]-$^{2}$H-cholesterol into the digestive system of the human subject by ingestion;
   c. waiting for from about 24 hours to about 96 hours;
   d. withdrawing a blood sample from the human subject;
   e. analyzing the blood sample by gas chromatography and mass spectroscopy and generating peak areas corresponding to the amount of [23,24,25,26,27]-$^{13}$C-cholesterol and the amount of [26,26,26,27,27,27]-$^{2}$H-cholesterol in the blood sample; and
   f. determining a percent cholesterol absorption by the further steps comprising:
      i. preparing a standard cholesterol tracer mole ratio curve;
      ii. correcting the peak areas corresponding to the amount of [23,24,25,26,27]-$^{13}$C-cholesterol and the amount of [26,26,26,27,27,27]-$^{2}$H-cholesterol from step (e);
      iii. identifying a serum tracer mole ratio corresponding to the corrected peak areas of step (ii) from the standard cholesterol mole ratio curve; and
      iv. dividing the serum tracer mole ratio by the ratio of the known molar amount of [23,24,25,26,27]-$^{13}$C-cholesterol introduced in step (a) and the known molar amount of [26,26,26,27,27,27]-$^{2}$H-cholesterol introduced in step (b).

2. The method of claim 1 wherein the administered mole ratio of [23,24,25,26,27]-$^{13}$C-cholesterol to [26,26,26,27,27,27]-$^{2}$H-cholesterol is from about 0.5 to about 5.0.

3. A method for inhibiting intestinal cholesterol absorption in a human subject who is a high absorber of cholesterol comprising the steps of:
   a. identifying that a human subject is a high cholesterol absorber by:
      i. introducing a known amount of a first metabolically stable cholesterol tracer into the blood stream of the human subject by injection;
      ii. introducing a known amount of a second metabolically stable cholesterol tracer into the human subject by ingestion;
      iii. waiting for from about 12 hours to about 5 days;
      iv. withdrawing a blood sample from the human subject; and
      v. analyzing the blood sample; and
   b. administering an effective amount of an intestinal cholesterol absorption blocker to the human subject who absorbs 50% or more of the second metabolically stable cholesterol tracer.

4. The method of claim 3 wherein the intestinal cholesterol absorption blocker is a pancreatic cholesterol esterase inhibiting agent.

5. The method of claim 4 wherein the pancreatic cholesterol esterase inhibiting agent is a sulfated polysaccharide.

6. The method of claim 4 wherein the pancreatic cholesterol esterase inhibiting agent is selected from group consisting of partially sulfated alginic acid, pectin, amylopectin, chitin, dextran, and cellulose.

7. The method of claim 4 wherein the pancreatic cholesterol esterase inhibiting agent is a 3-sulfated polysaccharide.

8. A method for measuring the ability of a human to adsorb cholesterol comprising the steps of:
   a. introducing a known molar amount of a first metabolically stable cholesterol tracer having a mass at least 5 daltons greater than a corresponding natural cholesterol into the blood stream of a human subject by injection;
   b. introducing a known molar amount of a second metabolically stable cholesterol tracer having a mass at least 5 daltons greater than a corresponding natural cholesterol into the human subject by ingestion;
   c. waiting for from about 12 hours to about 5 days;
   d. withdrawing a blood sample from the human subject;
   e. analyzing the blood sample by gas chromatography and mass spectroscopy and generating peak areas corresponding to the amount of the first metabolically stable cholesterol tracer and the amount to the second metabolically stable cholesterol tracer in the blood sample; and
   f. determining a percent cholesterol absorption by the further steps comprising:

i. preparing a standard cholesterol tracer mole ratio curve;

ii. correcting the peak areas corresponding to the amount of the first metabolically stable cholesterol tracer and the amount of the second metabolically stable cholesterol tracer from step (e);

iii. identifying a serum tracer mole ratio corresponding to the corrected peak areas of step (ii) from the standard cholesterol mole ratio curve; and iv. dividing the serum tracer mole ratio by the ratio of the known molar amount of the first metabolically stable tracer used in step (a) and the known molar amount of the second metabolically stable cholesterol tracer of step (b).

9. The method of claim 8 wherein the first or second metabolically stable cholesterol tracer is [23,23,25,26,27]-$^{13}$C-cholesterol.

10. The method of claim 8 wherein the blood sample is analyzed by gas chromatography and mass spectrometry.

11. The method of claim 8 wherein the first or second metabolically stable cholesterol tracer is [26,26,26,27,27,27]-$^{2}$H-cholesterol.

12. The method of claim 11 wherein the relative concentrations of the first metabolically stable cholesterol tracer and the second metabolically stable cholesterol tracer are corrected to obtain actual concentration data.

13. The method of claim 8 wherein from about 24 to about 96 hours are allowed to pass in step (c).

14. A method for inhibiting cholesterol absorption in a human subject who is a high absorber of cholesterol comprising the steps of:

a. identifying a human subject as high absorber of cholesterol by:
   i. introducing a known amount of [23,23,25,26,27]-$^{13}$C-cholesterol into the blood stream of the human subject by injection;
   ii. introducing a known amount of [26,26,26,27,27,27]-$^{2}$H-cholesterol into the digestive system of the human subject by ingestion;
   iii. waiting for from about 24 hours to about 96 hours;
   iv. withdrawing a blood sample from the human subject;
   v. analyzing the blood sample by gas chromatography and mass spectroscopy to find the relative concentrations of [23,23,25,26,27]-$^{13}$C-cholesterol and the [26,26,26,27,27,27]-$^{2}$H-cholesterol in the blood sample; and
   vi. correcting the relative concentrations from step (v) to obtain actual concentration data and to determine the percent cholesterol absorption; and b. administering an effective amount of a 3-sulfated polysaccharide to the human subjects who absorbs 50% or more of the [26,26,26,27,27,27]-$^{2}$H-cholesterol.

* * * * *